(12) United States Patent
Royse et al.

(10) Patent No.: US 7,276,024 B1
(45) Date of Patent: Oct. 2, 2007

(54) SURGICAL RETRACTOR

(75) Inventors: Alistair G Royse, Eltham (AU); David J Berry, Ringwood (AU); Michael R Kerr, Ivanhoe (AU); Brett I Hamilton, Warranwood (AU)

(73) Assignee: Research Surgical Pty Ltd., Victoria (AU)

( * ) Notice: Subject to any disclaimer, the term of this patent is extended or adjusted under 35 U.S.C. 154(b) by 501 days.

(21) Appl. No.: 10/333,950

(22) PCT Filed: Jul. 25, 2000

(86) PCT No.: PCT/AU00/00887

§ 371 (c)(1),
(2), (4) Date: Jan. 27, 2004

(87) PCT Pub. No.: WO01/06934

PCT Pub. Date: Feb. 1, 2001

(51) Int. Cl.
*A61B 1/32* (2006.01)
*A61F 2/00* (2006.01)

(52) U.S. Cl. ................................... 600/210
(58) Field of Classification Search .............. 600/213,
600/210, 219, 215, 201, 206, 222, 231, 232,
600/235
See application file for complete search history.

(56) References Cited

U.S. PATENT DOCUMENTS 4,627,421 A   12/1986   Symbas et al.
4,881,525 A * 11/1989   Williams .................... 600/219
5,052,373 A   10/1991   Michelson et al.
5,088,472 A    2/1992   Fakhrai
5,297,538 A *  3/1994   Daniel ........................ 600/206
5,697,891 A   12/1997   Hori et al.
5,931,777 A *  8/1999   Sava .......................... 600/213
6,309,349 B1* 10/2001   Bertolero et al. ........... 600/213

FOREIGN PATENT DOCUMENTS

DE    44 15 074        8/1985
FR    2 711 055        4/1995
GB    2 218 912 A     11/1989
WO    97/37596        10/1997

OTHER PUBLICATIONS

International Search Report—PCT/AU00/00887; ISA/AU, completed Aug. 8, 2000.

* cited by examiner

*Primary Examiner*—Pedro Philogene
(74) *Attorney, Agent, or Firm*—Harness, Dickey & Pierce, PLC

(57) ABSTRACT

A retractor for use in surgery, such as chest surgery, comprises two arms (4,6) each adapted to carry a blade (14,16) engageable with one side of an incision, the two arms (4,6) being connected by a pivot (8) at one end portion such that the arms (4,6) can be pivoted between a closed position and an adjustable open position in which the arms define a substantially V-shaped configuration in which the blades (14,16) maintain the sides of the incision in inclined relation. The arms are moved to the open position by means of a curved rack (20) carried by one of the arms (6) and a pinion (28) carried by the other arm (4), the pinion (28) being releasably lockable to retain the arms in the open position by a ratchet and pawl mechanism.

26 Claims, 3 Drawing Sheets

SURGICAL RETRACTOR

FIELD

This invention relates to retractors for use in surgery, and more particularly, but not exclusively, to retractors for use in chest surgery.

BACKGROUND

When a patient is incised for surgery, the sides of the incision are parted and are held apart by a retractor so that the surgeon has the required access to the patient's body. Conventionally, previously proposed retractors for chest surgery comprise two parallel arms, with blades disposed thereon to engage the sternum (breastbone). The operation of these retractors is such that the retractor arms remain parallel throughout their range of motion, resulting in the sides of the incision being parted by the same amount along the length of the retractor.

With particular regard to cardiac (heart) surgery, the ribs attached to the lower (inferior) portion of the sternum are longer and are provided with more cartilage and greater elasticity than the ribs attached to the upper portion of the sternum. This results in the upper (superior) ribs having less tolerance for displacement. The use of parallel-opening retractors for spreading the sternum for cardiac operations exerts greater force on the upper ribs, which may fracture. Another disadvantage of these retractors is that their use in spreading the sternum may result in excessive traction on the nerves (brachial plexus) leading to the patient's arm. Damage to these nerves can cause weakness or long term loss of feeling in the patient's ring and little fingers. One way to avoid applying excessive stress to the upper ribs is to position the retractor as low as possible. However, this approach does not allow the retractor to be placed in the most advantageous position for chest surgery and can cause damage to the sternum by having mainly the edges, rather than the full surfaces, of the blades exerting pressure on the sides of the incision.

During surgery, it is often necessary to open the incision both horizontally and vertically. Typically, two separate retractors have been required for this, one for the horizontal opening and another for the vertical opening. The applicant has determined that it would be beneficial to have a single retractor which could part the sternum with minimal displacement at the upper end and maximal displacement at the lower end, a "V"-shaped displacement, in both the horizontal and vertical planes.

SUMMARY

In accordance with the present invention, there is provided a retractor for use in surgery comprising two arms each adapted to carry a blade engageable with one side of an incision, the two arms being connected by a pivot at one end portion such that the arms can be pivoted between a closed position and an adjustable open position in which the arms to define a substantially V-shaped configuration in which the blades maintain the sides of the incision in inclined relation, and means for retaining the arms in the open position.

Preferably, each of the arms carries at least one sleeve rotatably mounted around the arm, the blade being mounted by the sleeve and the sleeve being lockable in a selected angular orientation whereby to change the angular orientation of the blade. This allows a V-shaped displacement of the retractor in both the horizontal and vertical planes.

Preferably, the blade is movable into a selected position along the arm. In one particularly preferred form there is an assembly of such sleeves on the arm lockable in end to end relation in a variable angular orientation and the blade is retained by co-operation between different pairs of adjacent sleeves to permit adjustment in blade position. The sleeves may also be interchangeably positioned on the arm to permit further adjustment of blade position.

Preferably, the blades are mounted by balls engaging within sockets formed by adjacent end faces of adjacent sleeves.

Preferably, the blades are replaceable and are available in a range of sizes.

Further according to the invention, there is provided a retractor for use in surgery comprising two arms each adapted to carry means engageable with the zone of an incision, the two arms being connected by a pivot at one end portion such that the arms can be pivoted between a closed position and an adjustable open position in which the arms define a substantially V-shaped configuration, and means for retaining the arms in the open position.

In one form the means engageable with the zone of an incision comprise means adapted to grip on the surface of an organ such as the heart.

DETAILED DESCRIPTION

The preferred embodiment of the invention will now be described, by way of example only, with reference to the accompanying drawings in which.

Figure 1:
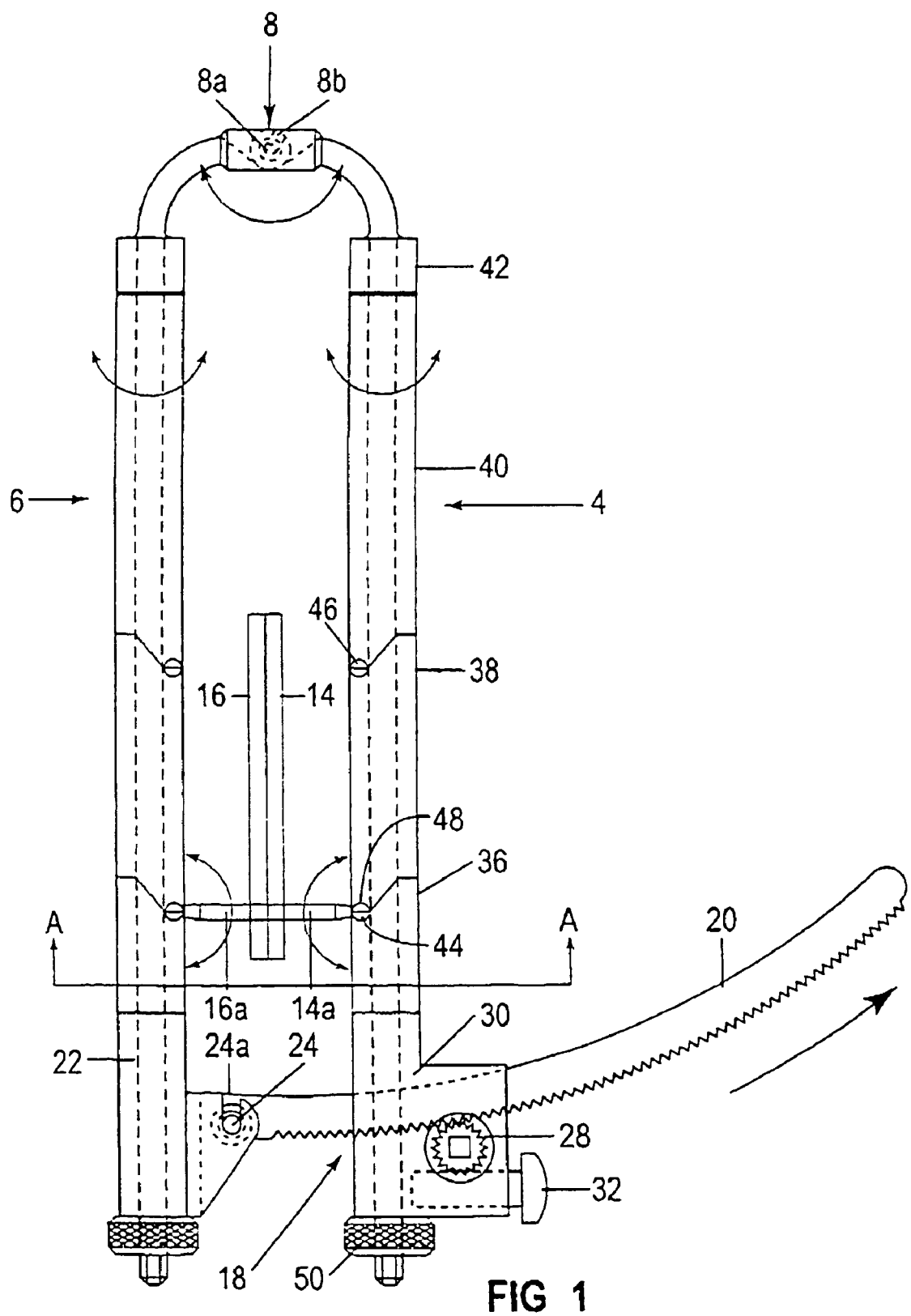
FIG. 1 is a top view of a preferred embodiment of a retractor in a closed position.
Figure 2:
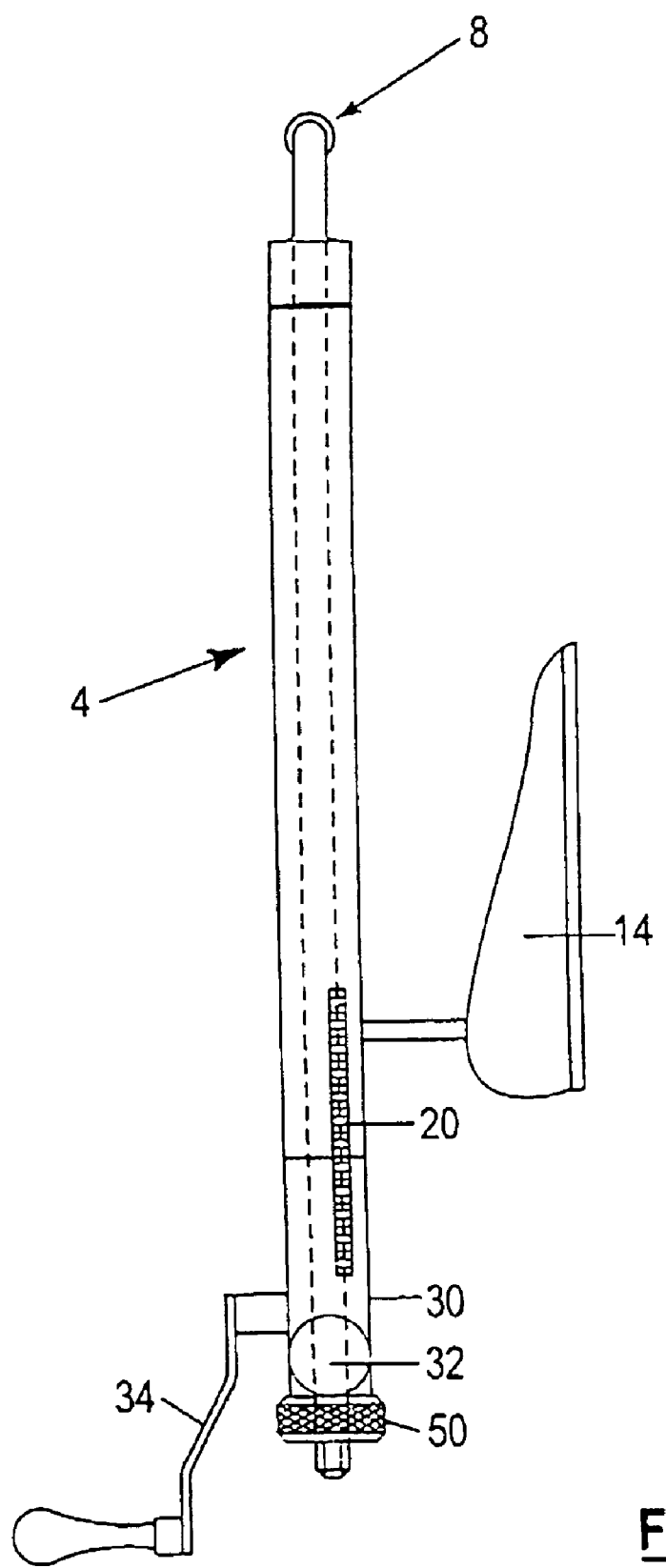
FIG. 2 is a right side view of the retractor illustrated in FIG. 1.
Figure 3:
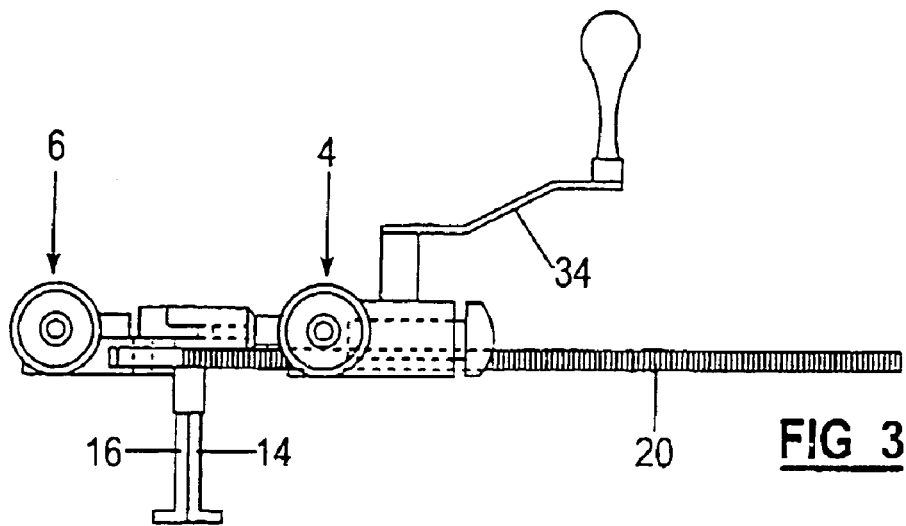
FIG. 3 is a front view of the retractor illustrated in FIG. 1.

The retractor in accordance with the preferred embodiment of the invention is principally for use in chest surgery and comprises two arms 4, 6 which are connected by a pivot 8 at their upper ends such that the arms 4, 6 can be pivoted between a closed position in which the arms are substantially parallel and an open position in which the arms 4, 6 are inclined to define a substantially V-shaped configuration. The arms 4, 6 each carry at least one blade 14, 16 for contact with tissue of the patient on either side of an incision such that opening of the arms 4, 6 opens the incision in a V-shape, the blades 14, 16 extending from the arms 4, 6 via support arms 14a, 16a rigidly connected to the blades. Preferably, the blades 14, 16 are replaceable and are available in a range of sizes to provide for various sizes and/or obesities of patients. The two arms 4, 6 are provided with locking means 18 to releasably hold the arms 4, 6 in a variable open position.

In the preferred embodiment, the locking means 18 includes an arm in the form of a curved rack 20, the curve being a circular arc centred substantially at the pivot 8. One end of the rack 20 is fixed to an end sleeve 22 of the arm 6 by a pivot 24. A toothed outer edge 26 of the rack 20 engages a driving pinion 28, rotatably mounted on an end sleeve 30 of the other arm 4, throughout a range of openings provided by the length of the rack 20. The pinion 28 is associated with a ratchet and pawl mechanism having a first "ratchet" state in which rotation of the pinion 28 in only one direction is allowed such that only opening movement of the arms 4, 6 is possible. A second "free" state allows both opening and closing movement of the arms 4, 6. The state of the mechanism can be changed by switching of a pawl release 32. The pinion 28 is drivable by means of a crank handle 34 in order to open the arms 4, 6 and hence to open the incision. The crank handle 34 is detachable from the pinion 28 to reduce interference during surgery.

The sleeve 30 is removably mounted on the arm 4. The arm 4 also carries further sleeves 36, 38, 40 between the sleeve 30 and a sleeve-like abutment 42 at the upper end portion of the arm 4. The sleeve 30 and adjacent sleeve 36 are engageable via serrations or other formations on their adjacent end faces in order to lock the sleeves 30, 36 against relative rotation. The adjacent end faces of the sleeve 40 and the abutment 42 also have similar serrations or other formations engageable to lock that sleeve 40 against rotation relative to the abutment 42. The end faces of the intermediate sleeve 38 and the adjacent faces of the sleeves 36 and 40 are shaped to cause rotational interlocking of the three sleeves 36, 38, 40. These adjacent interlocking faces of the three sleeves 36, 38, 40 are also configured to define sockets 44, 46 for receiving selectively a mounting ball 48 at the end of the support arm 14a carrying the blade 14. The assembly of the four sleeves 30, 36, 38, 40 on the arm 4 can be firmly secured to the arm 4 by means of a knurled nut 50 threadedly mounted at the lower end portion of the arm 4. When tightened the nut 50 will cause the uppermost sleeve 40 to be locked against the abutment 42 and due to the interengaging end surfaces of the other sleeves 30, 36, 38, the assembly of four sleeves 30, 36, 38, 40 will be firmly locked to the arm 4 against relative rotation. The ball 48 at the end of the support arm 14a carrying the blade 14 will also be firmly locked in the socket 44 or 46 between the sleeves 36, 38 by tightening the nut 50. By slackening the nut 50, the ball 48 can be removed from one of the sockets 44 or 46 between the sleeves 36 and 38 and relocated in the other socket 44 or 46 between the sleeves 38 and 40 in order to adjust the position of the blade 14 lengthwise of the arm 4 to suit a particular patient. Prior to final tightening of the nut 50, the ball 48 is able to be swiveled within the socket 44, 46 to facilitate adjustment in the orientation of the blade.

It is to be noted that the sleeves 36 and 40 are of different lengths and are capable of being interchangeably positioned on the arm 4 to provide the possibility of further options for the lengthwise positioning of the blade 14 on the arm 4.

A corresponding set of sleeves 22, 52, 54, 56 which act in the manner just described is mounted on the other arm 6. These sleeves also have the same range of adjustment in position to facilitate adjustment in the position of the blade 16 along the arm 6 and adjustment of its orientation by swiveling of its mounting ball within the socket defined by the interlocking faces of the adjacent sleeves.

All of the sleeves 22, 30, 36-40, 52-56 are removable from the two arms 4, 6 for cleaning purposes and the sleeves 22 and 30 are interchangeably mounted on the arms 4 and 6 in order to change the direction of projection of the rack 20. The handle 34 may engage the pinion 28 from either side allowing the sleeve 30 to be used on either arm 4, 6.

Figure 5:
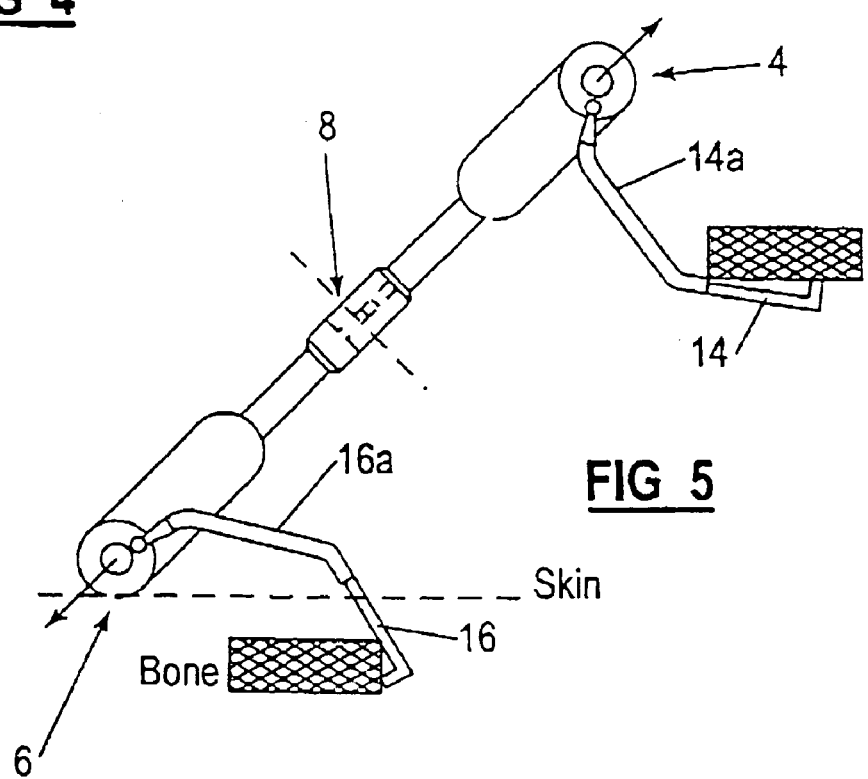
FIG. 5 is a section through A-A of FIG. 1 and showing how the retractor can be opened and inclined to hold one side of an incision higher than the other side.

When the nuts 50 are loosened, the angular positions of the sleeves 36-40, 52-56 on the arms 4, 6 can also be adjusted in order to change the angular orientation of the blades 14, 16 about the axis of the arms and the blades 14, 16 can be locked in their selected orientation by tightening the nuts 50 after adjustment of the angular position of the sleeves. This change in angular orientation may be necessary to suit the type of opening required by the surgeon. For example during chest surgery, the surgeon may require the incision to be opened not only horizontally but also one side of the incision to be lifted vertically relative to the other side to facilitate access (see FIG. 5). Thus the deep aspect of the chest wall on one side may be exposed, allowing access to the internal mammary (thoracic) artery for harvest. The adjustment in the angular position of the blades 14, 16 facilitates this.

Figure 4:
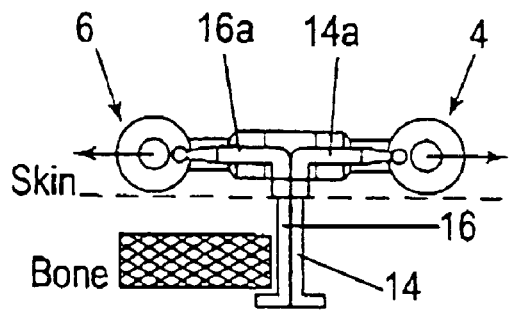
FIG. 4 is a section through A-A of FIG. 1.

Blades 14, 16 of differing design can be interchangeably mounted on the arms 4, 6 in order to adapt the retractor for different uses. FIG. 4, for example, illustrates blades with simple cranked legs and FIG. 5, for example, illustrates blades with legs of a more complex shape.

The retractor of the preferred embodiment in opening into a V-shaped configuration has the advantage of reducing the displacement of the upper portion of the chest during sternal surgery so that there is less risk of damage to the patient, in particular to the upper ribs and to the brachial plexus. The single retractor can be used to open the incision both vertically and horizontally, with the free end of the curved rack 20 extending in either direction, due to the interchangeability of the various components on the arms. The position of the blades 14, 16 can be altered to accommodate different sizes of chest and/or incision. Another advantage is the minimisation of extremities likely to cause interference during surgery. The retractor provides a rigidly held opening which offers improved access and vision to the surgeon.

The retractor can be completely disassembled for cleaning. As previously discussed, all of the sleeves are removable from the arms. The rack 20 is detachable from the sleeve 22 by sliding the pivot 24 of the rack 20 out of a slot-like pivot mounting 24a of the sleeve 22. The pivot 8 by which the two arms 4, 6 are pivotally connected consists of a pivot pin 8a on one of the arms releasably engageable in a slot-like pivot mounting 8b on the other of the arms, whereby the two arms can be disconnected by sliding the pin 8a out of the mounting 8b.

The pivot 24, in addition to allowing detachment of the rack 20, also provides limited freedom for movement of the rack 20 during use to permit ease of tension from the rack 20 and thereby ease of operation of the pawl release 32.

Optionally, clamps may be provided for application externally to the sleeves for specific applications such as valve retractor blades, beating heart stabilising devices, pericardial retractors, or holders for mister/blower devices.

The retractor described is not useable only for heart surgery but also is of benefit in other forms of surgery, for example abdominal surgery. A retractor in accordance with the invention designed specifically for abdominal surgery may have arcuately curved arms rather than straight arms as illustrated.

Although in the embodiment illustrated the arms mount the removable sleeves by which the blades are clamped, in alternative constructions provision for the removable sleeves may be omitted, with the arms being of a diameter such that blades can be clamped directly to the external surfaces of the arms. This construction will suffice in situations where the torque applied to the blades during use does not necessitate the mounting arrangement particularly described herein. In this form of the retractor, it is not necessary for the arms to be of circular cross-section and arms of other suitable form for the attachment of blades and other components can be provided, for example arms of rectangular cross-section or arms of flattened strip-like form.

A substantially smaller version of the retractor just described may be of benefit in other forms of surgery, such as "beating heart" surgery. In this version the arms do not carry retractor blades, but instead are of a generally flattened shape with small spikes, suction pads, and tape holders to grip on the surface of the heart and thereby to stabilise the segment of the surface of the heart defined between the two arms in their V-shaped open state. This form of retractor still includes the ratchet-type locking means 18 with the curved rack.

The embodiment has been described by way of example only and modifications are possible within the scope of the invention.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The invention claimed is:

1. A retractor for use in surgery comprising two arms each adapted to carry a blade engageable with one side of an incision, the two arms being connected by a pivot located at one end of the arms such that the arms can be pivoted between a closed position and an adjustable open position in which the arms define a substantially V-shaped configuration in which the blades maintain the sides of the incision in inclined relation, and means for retaining the arms in the open position located at an opposite end of the arms comprising a curved bar carried by one of the arms with the centre of curvature of the bar coinciding with the pivot, said curved bar co-operating with means carried by the other arm for releasably locking the bar relative to said other arm in a selected position to maintain the V-shaped configuration of the arms, and means for mounting the blades to the arms in selected positions along the length of the arms that are intermediate the pivot and the means for retaining the arms in the open position.

2. A retractor according to claim 1, wherein the curved bar is in the form of a toothed rack engageable with a driving pinion carried by the other arm, said driving pinion being rotatable to cause opening movement of the arms.

3. A retractor according to claim 2, comprising a removable handle engageable with the driving pinion for actuating the pinion.

4. A retractor according to claim 2, wherein the locking means comprises a ratchet and pawl mechanism operative to permit movement of the arms in an opening direction and to releasably lock the arms against movement in the closing direction.

5. A retractor according to claim 4, wherein the ratchet and pawl mechanism acts on the driving pinion to thereby releasably lock the pinion and thereby the rack in a position to prevent closing movement of the arms.

6. A retractor according to claim 5, further comprising retractor blades, and wherein said means for mounting the blades to the arms is further operable to mount the blades to the arms at selected angular orientations about the respective axes of the arms.

7. A retractor according to claim 6, wherein the means for mounting the blades comprises at least one sleeve rotatably mounted on each arm, the blades being mounted by the respective sleeves and the sleeves being lockable in selected angular orientations about the arms.

8. A retractor according to claim 7, comprising an assembly of said sleeves mounted on each arm and lockable in end-to-end relation in a variable angular orientation, the blade being clamped to the arm by co-operation between adjacent end faces of pairs of adjacent sleeves.

9. A retractor according to claim 8, wherein there are several such sleeves mounted on each arm and variation in blade position along the length of the arm is effected by clamping the blade between different pairs of said sleeves.

10. A retractor according to claim 9, wherein at least some of said sleeves are of different lengths and are interchangeably mountable on the arm in different positions to enable additional adjustment in blade position along the arm.

11. A retractor according to claim 8, wherein adjacent end faces of adjacent sleeves define a socket for receiving a mounting ball at the proximate end portion of an arm of the blade whereby to permit the arm to be swiveled within the socket and to be clamped in a selected angular position.

12. A retractor according to claim 8, wherein each arm includes a screw device actuable to clamp the assembly of sleeves in end-to-end relation in a selected angular orientation about the arm.

13. A retractor according to claim 8, wherein the rack is carried by a further said sleeve removably mounted on the said one arm and the driving pinion and ratchet and pawl mechanism is carried by a further said sleeve removably mounted on the other of said arms, each of said further sleeves lying in end-to-end relation with the said assembly of sleeves on the associated arm.

14. A retractor according to claim 1, wherein the pivot is demountable to permit detachment of the two arms for cleaning purposes.

15. A retractor according to claim 1, wherein the arms are substantially straight and are substantially parallel in a closed condition of the retractor.

16. A retractor according to claim 1, wherein the arms are arcuately curved.

17. A retractor according to claim 1, further comprising retractor blades adapted to be clamped to the external surfaces of the retractor.

18. A retractor according to claim 1, further comprising retractor blades adapted to be clamped to the external surfaces of the arms.

19. A retractor according to claim 7, further comprising retractor blades adapted to be clamped to the external surfaces of the sleeves.

20. A retractor for use in surgery, the retractor having a first end portion and a second end portion and comprising two arms each adapted to carry means engageable with the zone of an incision, the two arms being connected by a pivot located at the first end portion such that the arms can be pivoted between a closed position and an adjustable open position in which the arms define a substantially V-shaped configuration, and means for retaining the arms in the open position comprising a curved bar carried by one of the arms at the second end portion and opposite from the pivot, with the centre of curvature of the bar coinciding with the pivot, said curved bar co-operating with means carried by the other arm for releasably locking the bar relative to said other arm in a selected position to maintain the V-shaped configuration of the arms and wherein said means engageable with the zone of an incision are carried by the arms at a location intermediate the first end portion and the second end portion.

21. A retractor according to claim 20, wherein the means engageable with the zone of an incision comprise retractor blades.

22. A retractor according to claim 20, wherein the means engageable with the zone of an incision comprise means adapted to grip on the surface of an organ such as the heart.

23. A retractor according to claim 20, wherein the curved bar is in the form of a toothed rack engageable with a driving pinion carried by the other arm, said driving pinion being rotatable to cause opening movement of the arms.

24. A retractor according to claim 20, wherein the means for releasably locking comprises a ratchet and pawl mechanism operative to permit movement of the arms in an opening direction and to releasably lock the arms against movement in the closing direction.

25. A retractor for use in surgery comprising:
first and second arms, each of the first and second arms having a first end and a second end, the first and second arms being joined at their respective first ends by a pivot;
the pivot enabling the first and second arms to rotate between a closed position in which the arms are substantially parallel and an open position in which the arms define a substantially V-shape;
an opening mechanism located at the respective second ends of the first and second arms and operable to move the arms between the closed position and the open position;
a lock located at the second end of at least one of the first and second arms and operable to maintain the arms in the open position; and
a blade mounted to at least one of the first and second arms at a location along the length of the at least one of the first and second arms that is intermediate the pivot and the lock, the blade adapted to engage one side of a surgical incision.

26. The retractor of claim 25 wherein:
the opening mechanism comprises a toothed rack carried by one of the first and second arms and a rotatable pinion carried by the other one of the first and second arms, the pinion engaging the toothed rack such that rotation of the pinion causes movement of the rack; and
the lock comprises a comprises a ratchet and pawl mechanism that permits movement of the pinion in a opening direction and releasably retains the pinion against movement in a closing direction.

* * * * *